United States Patent [19]

Marshall, III

[11] 4,152,596
[45] May 1, 1979

[54] APPARATUS FOR REDUCING PULSE PILEUP IN AN ELEMENTAL ANALYZER MEASURING GAMMA RAYS ARISING FROM NEUTRON CAPTURE IN BULK SUBSTANCES

[75] Inventor: J. Howard Marshall, III, Pasadena, Calif.

[73] Assignee: MDH Industries, Inc., Monrovia, Calif.

[21] Appl. No.: 812,769

[22] Filed: Jul. 5, 1977

[51] Int. Cl.² .......................................... G01N 23/00
[52] U.S. Cl. ............................... 250/358 R; 250/390; 328/117
[58] Field of Search ............... 250/390, 391, 392, 302, 250/303, 308, 270, 362, 358 R

[56] References Cited
U.S. PATENT DOCUMENTS

| 3,025,400 | 3/1962 | Schultz | 250/302 |
| 3,508,047 | 4/1970 | Mott et al. | 250/391 X |
| 3,508,048 | 4/1970 | Starnes | 250/362 |

Primary Examiner—Davis L. Willis
Attorney, Agent, or Firm—Arthur V. Doble

[57] ABSTRACT

The active reduction of the number of analyzed events with pulse amplitudes which pileup has distorted improves measurement accuracy and response time in an apparatus for neutron-capture-based on-line elemental analysis of bulk substances. Within the apparatus, the analyzed bulk substance is exposed to neutrons, and neutron capture generates prompt gamma rays therefrom. A detector interacts with some of these gamma rays to produce electrical signals used to measure their energy spectrum by pulse-height analysis. Circuits associated with this pulse-height analysis also detect the pileup of the signals of two or more independent gamma rays using one or more of several techniques. These techniques include multiple outputs from a special amplifier-discriminator system, which has been optimized for low pulse-pair resolving time and may have adaptive thresholds, and the requirement that the relative amplitudes of the outputs of slow and fast amplifiers be consistent with a single event producing both outputs. Pulse-width measurements are also included in the pileup detection.

23 Claims, 3 Drawing Figures

BLOCK DIAGRAM - SENSOR ELECTRONICS

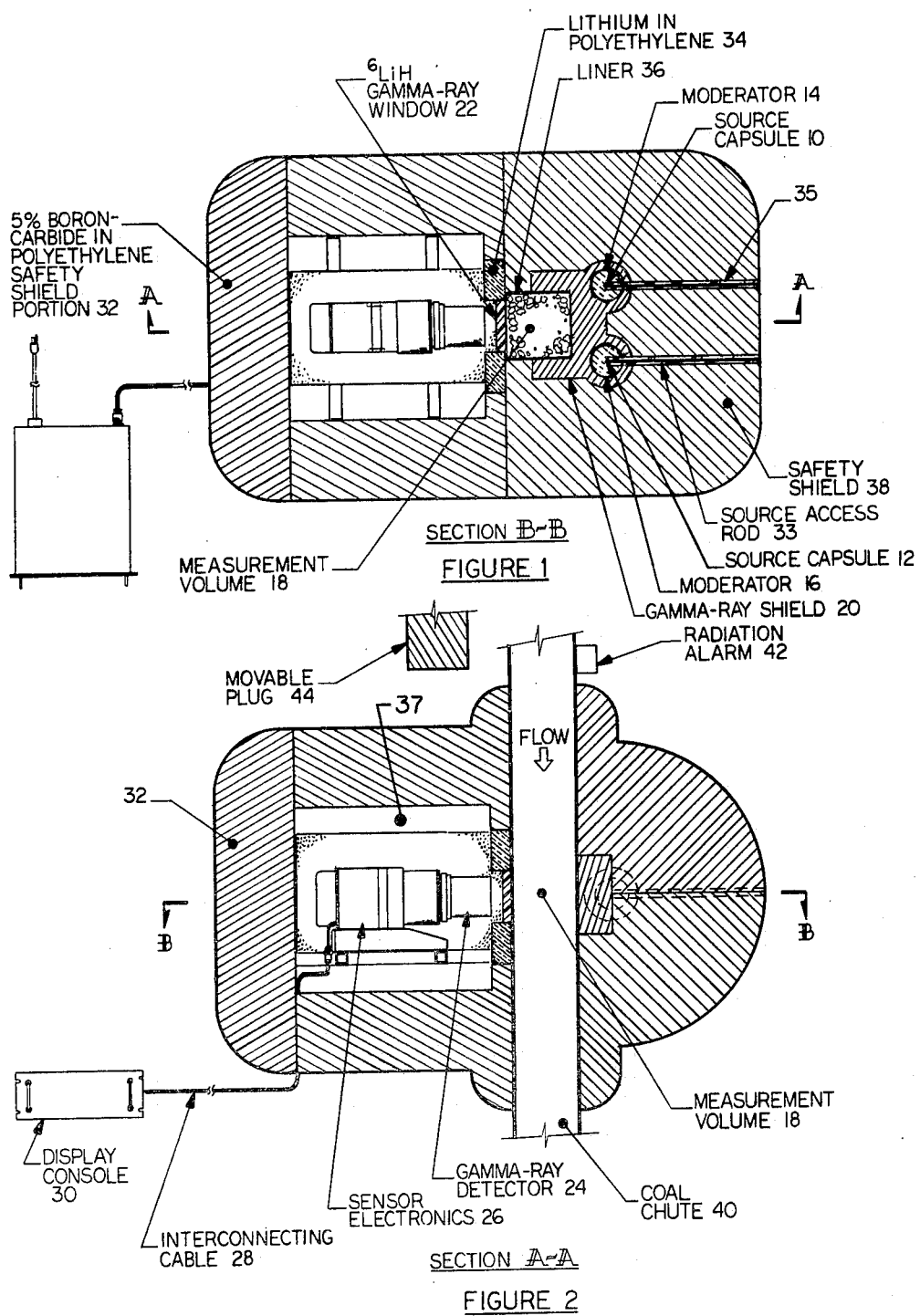

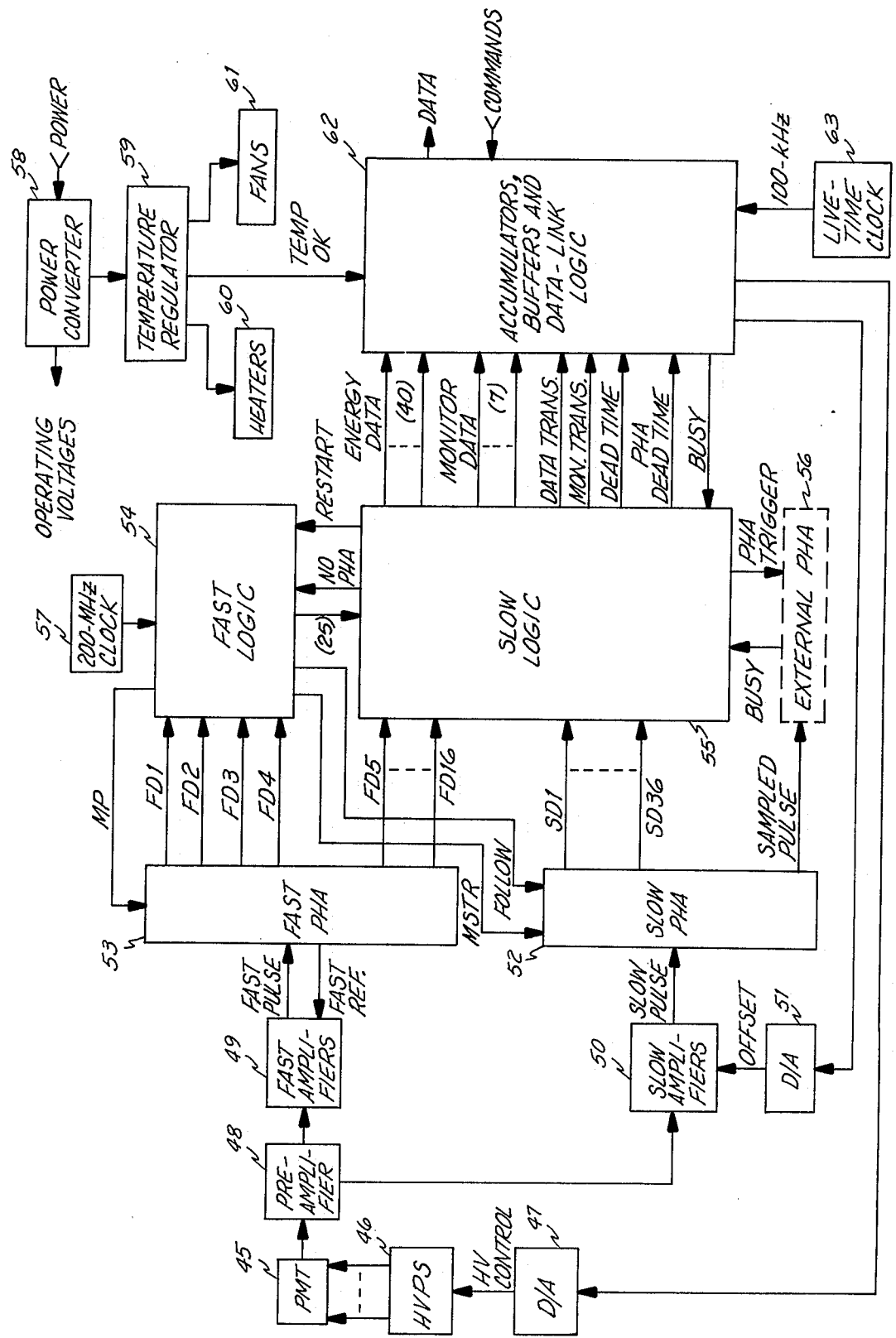
FIGURE 3 BLOCK DIAGRAM—SENSOR ELECTRONICS 26

APPARATUS FOR REDUCING PULSE PILEUP IN AN ELEMENTAL ANALYZER MEASURING GAMMA RAYS ARISING FROM NEUTRON CAPTURE IN BULK SUBSTANCES

BACKGROUND OF THE INVENTION

1. Field of the Invention

This invention generally relates to nuclear meters, and particularly to an apparatus or a method for reducing the deleterious effects caused by pulse pileup in a neutron-capture-based elemental analyzer for on-line measurement of bulk substances.

2. Description of the Prior Art

The rising cost of fuels, coupled with the need to avoid atmospheric pollution when burning them, has led to the requirement that their composition be known at various points in the fuel-preparation cycle. For example, because of the scarcity of low-sulfur crude oils and the cost of sulfur removal, the value of fuel oil increases significantly as its sulfur content becomes lower, indicating that accurate fuel-oil blending to a fixed sulfur level consistent with allowable amounts of pollution is both cost effective and an efficient utilization of increasingly-scarce hydrocarbons. Furthermore, precise knowledge of the heat content of fuel oil allows furnaces and boilers to be operated in a more efficient manner. In addition, knowledge of the amount of sulfur and other contaminants such as vanadium and nickel in various hydrocarbon streams can help prevent the poisoning of catalysts used in oil refineries, avoiding costly shut downs.

In the case of coal, sulfur content is generally higher than that of oil, making the pollution problem even more severe. As a result, expensive coal-cleaning plants, stack-gas scrubbers and precipitators are necessary, all of which can be operated more efficiently if the coal composition is known on a real-time on-line basis. Efficient boiler operation also benefits from this composition measurement, and knowing the composition of the ash in the coal can be used to avoid boiler slagging, which is a costly problem that is generally absent for fuel oil.

Particularly in the case of coal, but also for oil, these composition measurements have to be made on inhomogeneous substances with high mass flow rates and variable compositions. Thus, this measurement should continuously reflect the average composition of the bulk substance, and response times should be fast enough to permit effective process control. Generally the latter requirement implies a speed of response ranging from a few minutes up to an hour.

A technique which can satisfy these requirements can often be used in applications which do not involve fuels or their derivatives. For example, it could measure the nitrogen content of wheat in order to determine the amount of protein present, which in turn is related to food value. Thus, the measurement of fuels is illustrative only and is not essential to this invention, which applies to all measurements of bulk substances by the techniques to be described hereinafter.

Several methods for composition measurement are known in the prior art, the most obvious one being sampling followed by chemical analysis. This technique provides most present data on the composition of various bulk substances. Unfortunately sampling is inherently inaccurate because of the lack of homogeneity of bulk materials, and large continual expenditures for manpower, sampling devices and chemical-analysis equipment are required to provide response times which at best could approach one hour. These disadvantages lead to the consideration of other techniques which are faster, more subject to automatic operations and more of an on-line continuous bulk measurement.

One technique often used in industrial environments for elemental analysis involves X-ray fluorescence. This technique relies on the fact that each atom emits X rays with distinct and well-known energies when external radiations disturb its orbital electrons. Unfortunately, sulfur, which is an interesting element from the standpoints of air pollution and catalyst poisoning, emits mostly 2-keV X rays, which can only traverse about 0.1 mm of a typical fuel. Iron, which is one of the elements generating the highest-energy X rays in coal, produces mostly a 6-keV X ray, which also cannot escape from any appreciable amount of coal or other nongaseous fuel. Thus, the use of X-ray fluorescence for other than gaseous materials requires either the preparation or the vaporization of a sample in an atmosphere which does not confuse the measurement. In either case, a difficult sampling and sample-preparation problem compounds the errors associated with X-ray fluorescence itself.

A second technique usually involving X rays which are more penetrating is X-ray absorption. In this case one measures the differences in the absorption or scattering of X rays caused by changes in the amounts of certain elements. In the case of relatively-pure hydrocarbons such as refined fuel oil, this technique can provide a useful measurement of sulfur content because sulfur at X-ray energies near 22 keV can have a predominant effect on the X-ray absorption. This predominance, however, is dependent on the lack of most of the metals which are present in coal and may also be present in oil. In addition, 22-keV X rays only penetrate about 2 mm in most non-gaseous fuels, making sampling still a requirement. Moreover, this technique is generally limited to measuring only one of several potentially interesting elements, and the measurement of the relative amounts of many different elements in a complex mixture such as coal becomes difficult.

Nonetheless, nuclear techniques in general remain attractive because they often can be automated and in principal do not require actual manipulation of the bulk material itself. The problems with X-ray fluorescence and absorption arise partly because the associated radiations are not sufficiently penetrating. However, because the energetic gamma rays produced by the capture of thermal neutrons will penetrate over 100 mm of most fuels, an analysis technique based on them can provide an accurate, continuous, on-line measurement of the elemental composition of bulk substances without sampling.

This technique is based on the fact that almost all elements when bombarded by slow neutrons capture these neutrons at least momentarily and form a compound nucleus in an excited state. Usually the prompt emission of one or more gamma rays with energies and intensities which are uniquely characteristic of the capturing nucleus dissipates most of this excitation energy. Because these prompt gamma rays often have energies in the 2- to 11-MeV range, they can penetrate substantial quantities of material to reach a gamma-ray detector and its associated electronics which provide a measurement of their energy spectrum. Thus, for those isotopes with significant capture cross sections and prominent gamma-ray lines, measurement of the number of prompt gamma rays present at various energies can be used to determine in an on-line, real-time basis the quantity of most of the elements present in bulk substances, which can be flowing through the analyzer.

Although these techniques have been used in the laboratory under controlled conditions, their implementation in an automatic, on-line instrument placed in an industrial environment presents unique problems. One of these problems results from the need to provide simultaneously a fast speed of response and good accuracy. Because counting capture gamma rays is a random process, it is subject to statistical variations. These variations produce fluctuations in the measured elemental compositions, which decrease as the number of detected events increases. Thus good accuracy requires large numbers of detected events, which in turn requires high counting rates and/or long counting times. As a result, a fast speed of response together with acceptable statistical fluctuations requires high counting rates. High counting rates, however, then lead to problems with pulse pileup as discussed hereinafter.

The minimization of systematic errors in the composition measurement requires that the energy of the detected capture gamma rays be measured with good resolution. For both semiconductor and scintillation gamma-ray detectors, good energy resolution implies that pulse amplifiers must convert the detector pulses into amplifier pulses with widths in the range from $2 \times 10^{-7}$ s to $10^{-5}$ s. These relatively-long pulses are necessary to filter noise, which can originate either in the amplifiers themselves or in the gamma-ray detector, and to collect the majority of the charge produced by the detector in response to a gamma-ray interaction.

However, during this integration or filtering interval a subsequent event could produce an additional output from the gamma-ray detector, and this pulse could then add to the one already being processed in the pulse amplifier. The resultant combined pulse exemplifies "pulse pileup" in that it is the result of two or more pulses piling up on each other to generate a combined pulse which does not represent the energy of any of the individual detected events. Including such pileup events in the spectral measurement adds to errors in the composition measurement, and, as counting rates are increased to reduce statistical fluctuations and/or response time, pileup events rapidly cause excessive errors. Thus the desire for good accuracy and a fast speed of response inevitably leads to some form of pileup detection which permits the removal of most of the pileup events from the measured energy spectrum. As this pileup detection becomes more efficient, then counting rates can be increased accordingly, resulting in reduced statistical fluctuations and/or response times.

Typically pileup-detection schemes involve two amplifier chains processing the same detector signal with different response times. The slow-amplifier chain produces pulses with widths which give good energy resolution, and its output is used for the measurement of the energy spectrum of the capture gamma rays. The fast-amplifier chain on the other hand produces a much-narrower pulse used primarily to define the time of arrival of an event. Thus, if circuits observing the output of the fast-amplifier chain determine that two or more events arrived during the interval lasting from the time of arrival of the first pulse until the time when the energy measurement is no longer sensitive to pulse pileup, then the output of the slow-amplifier chain can be ignored for such an event, reducing pileup-induced errors.

In the prior art the output pulse from the fast-amplifier chain was applied to a single discriminator with a fixed threshold. This circuit converted the fast pulse into a digital signal which was high for the entire interval during which the fast pulse exceeded the threshold. The transition at the leading edge of this digital signal approximately defined the event-arrival time. If two events producing fast pulses exceeding the discriminator threshold arrived at times separated by an interval which was larger than the time which the discriminator output remained high from the first event, they would be recognized as distinct events. If only one event was detected during an integration interval defined by noise and accuracy criteria, then for a selected range of pulse amplitudes a linear gate was opened, and the detector signal was integrated during that interval. Subsequent pulse-height-analysis circuits then determined the size of this integrated signal to provide the energy-spectrum measurement. The gated integrator and the pulse-height-analysis circuits constituted the slow-amplifier chain in this case.

Although this technique rejected many pileup events, it had several disadvantages leading to poorer accuracies and/or response times. One such disadvantage resulted from the fact that amplifier noise and/or fluctuations in the detector output signal limited the narrowness of the fast pulse used for event detection. For such a pulse with a non-zero width, a single discriminator as used in the prior art could not distinguish events arriving closer together in time than nearly the full width of this pulse. In addition, because those events with amplitudes below the discriminator threshold were not detected at all, they contributed to pileup-induced errors just as if no pileup rejection was present. As the discriminator threshold was reduced to decrease the number of these events, then generally the fast pulse had to be made wider to avoid false alarms caused by noise. As a result the inherent effectiveness of the pileup rejection in the prior art was overly limited, and tolerable counting rates were lower than desired.

The choice of the optimum threshold became even more complicated for scintillation gamma-ray detectors where statistical variations in the photocathode current during the scintillation process was the principal noise source. As a result the optimum discriminator threshold depends on the energy of the detected event, and the prior-art systems had no provision for implementing this energy-dependent optimization.

An additional problem with prior-art systems arose from their use of linear gates followed by relative-slow pulse-height analyzers. This technique had acceptable dead times only if a second discriminator observing the fast pulse permitted the linear gate to open only for a small fraction of the number of detected events. This restriction required that only the portion of the energy spectrum with low counting rates could be analyzed if live time was to remain high in order to keep statistical fluctuations low. However, in general this restriction is undesirable because high-counting-rate portions of the energy spectrum also contain useful information.

SUMMARY OF THE INVENTION

Applicant herein has conceived of an invention for overcoming these problems present in the prior-art systems. The invention may be embodied in any of several forms without limiting the scope thereof. Basically the prior-art systems cannot provide a pulse-pair resolving time which is much less than the full width of the output pulse from the fast-amplifier chain. Because electronic noise and statistical fluctuations inherently limit the narrowness of this pulse, more-sophisticated means than a single discriminator are necessary if pulse-pair resolving times are to be improved. The use of several discriminator thresholds is one method for improving pulse-pair resolving times. For practical fast pulses with non-zero rise and fall times, sometimes events which arrive so closely together that the fast pulse continually exceeds the lowest discriminator threshold will produce more than one positive transition at the output of a discriminator with a higher threshold. Thus if multiple transitions at any of several thresholds can result in pileup detection, the pulse-pair resolving time will be less than that associated with only a single threshold, which must be at a low value in order to prevent low-energy events from escaping pileup detection. Because pulses are wider near the baseline than at higher amplitudes, the lowest threshold will invaribly have the longest pulse-pair resolving time, leading to poorer performance in the prior-art systems.

The use of multiple fast thresholds for pileup detection has an additional advantage for scintillation gamma-ray detectors using photomultiplier tubes. In that case multiple pulses at the output of one or more of the discriminators with low thresholds can be ignored after the event has been detected. This technique can effectively raise the threshold for pileup detection following a large-amplitude detector pulse which produces large statistical fluctuations in the current from the photomultiplier. Because these fluctuations can simulate separate low-energy events which often cannot be distinguished from pileup, high-energy events will generally reject themselves for low pileup-detection thresholds. In the prior-art systems the rejection threshold had to be high enough to avoid this self-veto phenomenon, leading to the unfortunate acceptance of unnecessary pileup for low-energy events. However, allowing the pileup-rejection threshold to adapt to the measured pulse amplitude avoids the need to compromise the pileup rejection at low energies in order to avoid the self-veto of high-energy events.

A further improvement in pileup rejection can result from the measurement of the width of the discriminator pulse. Even though two events arrive within a time which is too short to produce multiple positive transitions at the discriminator output, they may cause the width of the discriminator output pulse to be noticeably longer than that expected for a single pulse. Thus long discriminator pulses can be used to indicate pulse pileup, yielding pulse-pair resolving times which are shorter than those obtained purely by looking for multiple positive transitions. If the fast pulse has non-zero rise and fall times, the width threshold for pileup detection can depend on the measured pulse amplitude in order to allow for the fact that large-amplitude pulses will have wider discriminator pulses than small-amplitude pulses.

Similarly multiple pulses arriving at nearly the same time may produce a peak pulse amplitude from the fast-amplifier chain which does not bear the same relationship to the amplitude of the pulse from the slow-amplifier chain that a single pulse produces. This difference results because the pulses must arrive much closer together for nearly perfect summing to occur in the fast-amplifier chain than in the slow-amplifier chain. Thus, the slow pulse may represent nearly the perfect addition of the energies of the two events, whereas the peak amplitude of the fast pulse may be considerably less. As a result, pileup often can still be detected for pulses arriving within a time which is too short to produce multiple discriminator transitions by observing that the peak amplitude of the fast pulse is too small compared to the slow pulse to be consistent with only one pulse being present.

One method of implementing this correlation check between the fast and slow pulses involves the use of multiple discriminators, some of which are connected to the output of the slow-amplifier chain and others are connected to the fast-amplifier chain. Then simple digital gates appropriately connected between these two sets of discriminators can provide the check of amplitude correlation. The discriminators processing the slow pulse can also provide the energy-spectrum measurement, avoiding the dead time involved in the slow pulse-height analyzers used in the prior art. As a result the analysis dead time is limited only by the width of the slow pulse required to obtain the desired energy resolution.

The use of multiple fast discriminators, pulse-width measurement and amplitude-correlation checks are all independent methods for improving pulse-pair resolving times. In addition one or more of these methods can be combined in order to achieve event better performance.

The present invention has several features of novelty over the known prior art, including the use of specific techniques to improve the rejection of pulse pileup in an on-line elemental analyzer detecting neutron-capture gamma rays in order to increase measurement accuracy and reduce response times.

It is an object of this invention to provide an improved apparatus for detecting and rejecting events with pulse heights which have been distorted by pileup.

It is a further object of this invention to provide an improved apparatus which has a pulse-pair resolving time which is less than the width of the amplifier pulses.

It is an additonal object of this invention to process the signals from a gamma-ray detector in an on-line elemental analyzer in a manner which minimizes pulse pileup and dead time.

For a better understanding of the present invention, together with other and further objects thereof, reference is made to the following description taken in connection with the accompanying drawings in which preferred embodiments of the invention are illustrated, the scope of the invention being pointed out and contained in the appended claims.

BRIEF DESCRIPTION OF THE DRAWINGS

FIG. 1 shows a cross-sectional view of a meter for the elemental analysis of coal. Included therein are the sensor electronics, in which is contained a preferred embodiment of this invention.

FIG. 2 shows further details of the same instrument as that shown in FIG. 1, but in this case the section view has been taken along the line A—A in FIG. 1. The line B—B of FIG. 2 shows the sectioning line used for producing FIG. 1.

FIG. 3 shows the functional blocks contained in the sensor electronics shown in FIGS. 1 and 2 and provides more detail of a preferred embodiment of this invention.

DESCRIPTION OF THE PREFERRED EMBODIMENTS

The application of these methods to the elemental analysis of coal forms one of the preferred embodiments of this invention, as shown in the Figures. Other embodiments involve the on-line measurement of coal-water mixtures, coal-oil mixtures, crude oil, fuel oil, gasoline, wheat and most other bulk substances containing some hydrogen. Thus, the portions of the preferred embodiment shown in the Figures which are specific to the measurement of coal are illustrative only and are not intended to limit the scope of this invention.

The instrument contains the bulk substance to be analyzed, which may flow through the instrument in order to provide a continuous, on-line measurement of bulk composition. In the embodiment shown in FIGS. 1 and 2, the coal is confined in the centrally-located measurement volume 18 which is the region throughout which the composition measurement takes place. Coal passing through the coal chute 40 continuously fills the measurement volume 18 with a current coal sample, facilitating the desired continuous, on-line bulk measurement.

The instrument also includes a source of neutrons, which in the embodiment shown in FIG. 1 consists of two capsules 10 and 12 containing the isotope Californium-252. In this embodiment neutron moderators 14 and 16 surround the source capsules 10 and 12 in order to reduce neutron energies before the neutrons enter the measurement volume 18. A gamma-ray shield 20 then surrounds the moderators 14 and 16 to absorb gamma rays produced by the source and the moderators and to provide a material with low neutron absorption through which neutrons can diffuse away from the source. The use of the moderators and gamma-ray shield and an isotopic neutron source are not essential to this invention, and their use in the embodiment shown in FIGS. 1 and 2 is not intended to limit the scope of the invention.

In the preferred emobodiment shown in FIGS. 1 and 2, the neutron sources 10 and 12 are outside of the measurement volume 18, indicating that most neutrons will not enter the measurement volume 18. In order to control these unused escaping neutrons to avoid a radiation hazard and background in the measured energy spectrum, the preferred embodiment shown in FIGS. 1 and 2 includes the $^6$LiH gamma-ray window 22, the boron-doped-polyethylene safety shields 38 and 32 with the source access rods 33 and 35, the lithium in the polyethylene 34 and the liner 36 for the measurement volume 18. The existence of these neutron-absorbers in the preferred embodiment of FIGS. 1 and 2 is not intended to limit the scope of this invention.

In order to avoid a radiation hazard from escaping neutrons when the measurement volume 18 is empty, in the preferred embodiment the shield 32 on the detector side of the measurement volume 18 has been placed behind the sensor electronics 26 such that the gamma-ray detector 24 and the sensor electronics 26 are located within a chamber 37 in the neutron absorber. Even in this configuration some scattered radiation can leave the top and the bottom of the coal chute 40 passing through the measurement volume 18 when it is empty, because this region is not covered by shielding. A radiation alarm 42 and/or a movable plug 44 for the coal chute 40 when no coal is present provide the necessary protection to personnel when the coal chute is empty. Their existence and the presence of a chamber 37 for the sensor electronics 26 in the preferred embodiment are not intended to limit the scope of this invention.

Some neutrons will diffuse through the gamma-ray shield 20 into the measurement volume 18. There hydrogen present in the coal being analyzed will moderate them further, and then they often will be captured by the various nuclei present in the analyzed coal. These neutron-capture reactions generally produce gamma rays, which travel outward in all directions. Some of these gamma rays will travel through the measurement volume 18 and the neutron-absorbing gamma-ray window 22 and enter the gamma-ray detector 24 shown in FIG. 2.

In the preferred embodiment shown in FIGS. 1 and 2, this detector 24 is a large NaI(Tl) crystal, although other detectors such as CsI(Tl), CsI(Na), Ge or Ge(Li) could be used in instruments incorporating the features of this invention. The invention also is not limited to the case of a single gamma-ray detector, as shown in FIGS. 1 and 2, and the principles of the invention apply equally well to instruments containing several detectors, which may be all the same type or a combination of types.

When the gamma rays interact in the gamma-ray detector 24, they produce electrical signals indicative of their energy. The sensor electronics 26 convert these electrical signals into digital information, which is transmitted over an interconnecting cable 28 to the display console 30. The display console 30 processes this information using the fact that neutron capture produces an energy spectrum which depends on the amounts of the various elements capturing the neutrons. The result of this processing is information concerning the relative concentrations of the various elements of interest in the measurement volume 18 and any other properties, such as density, which may be usefully obtained from the measured spectrum.

The sensor electronics 26, which are illustrated in greater detail in FIG. 3, contain the pileup-rejection circuits constituting an essential part of this invention. In this embodiment the gamma rays interact in the NaI(Tl) crystal of detector 24 to produce light pulses detected by the photomultiplier tube (PMT) 45. These light pulses cause the photomultiplier 45 to produce current pulses with a charge related to the gamma-ray energy. The pulse-shaping amplifiers 48, 49 and 50 convert the photomultiplier 45 current pulses into voltage signals optimized for either good time resolution or good charge resolution. The fast pulses with the good time resolution but poor charge resolution enter the fast pulse-height analyzer (PHA) 53, whose outputs are used by the fast logic 54 and the slow logic 55 to define events which are usually uncontaminated by pulse pileup. The slower pulses with good charge resolution enter the slow PHA 52, which defines the boundaries of the energy windows used for the determination of the amounts of various elements present in the coal. When the logics 54 and 55 accept the event, they record the outputs of the fast PHA 53 and the slow PHA 52 and cause a count to be added to the appropriate accumulator contained in the accumulators, buffers and data-link logic 62. Periodically the data contained in these accumulators are read out serially through various shift registers to the encoding circuits for the data link. They then pass as a transition code over the cable 28 shown in FIG. 1 to the remotely-located display console 30.

The sensor electronics 26 also contain a high-voltage power supply (HVPS) 46, which generates the operating voltages for the photomultiplier 45 and thus controls its gain. A digital-to-analog converter (D/A) 47 then permits digital commands from the display console 30 to vary the output of the high-voltage supply 46 in order to hold the system gain fixed using methods which do not constitute a part of this invention. A second digital-to-analog converter 51 provides a similar stabilizing function for the offset voltage of the slow amplifiers 50, and this converter 51 also does not constitute a part of this invention.

The sensor electronics 26 operates at a fixed temperature which is controlled by the temperature regulator 59 using heaters 60 and fans 61. A power converter 58 supplies the operating voltages required by the various circuits in the sensor electronics 26.

Returning to a description of the pileup-rejection circuits which embody this invention, we begin with the current pulse leaving the photomultiplier 45. This pulse is relatively slow because of the inherent response time of NaI(Tl), and a combination of various amplifier types is necessary to convert this pulse into ones of suitable shape for the fast PHA 53 and the slow PHA 52. Fast-amplifier means and slow-amplifier means provide this amplification and pulse shaping. The fast-amplifier means includes the fast amplifiers 49 and part of the preamplifier 48. In the embodiment shown in FIG. 3, the preamplifier 48 produces a voltage pulse with nearly the same shape as the current pulse fom the photomultiplier 45 and also generates a current pulse which enters the slow amplifiers 50. The use in this embodiment of a single preamplifier 48 which forms a part of both the fast-amplifier means and the slow-amplifier means is not intended to limit the scope of this invention.

The fast amplifiers 49 produce the fast pulse, which has a width of 37 ns at one half of its peak amplitude. This pulse also crosses the baseline slightly to provide a well-defined width of 63 ns at 10% of its peak amplitude. The fast pulse has been optimized to produce good pulse-pair resolving times at the expense of energy or amplitude resolution.

The slow-amplifier means, which includes part of the preamplifier 48 and slow amplifiers 50, produces the slow pulse. These amplifiers use delay lines to generate a bipolar pulse with a 250-ns integration time, which is sufficient to obtain acceptable energy resolution. The pulse returns to the baseline in less than 700 ns to the point where a second event could be analyzed without amplitude distortions. This width is the primary factor in defining analysis live time, which is monitored in the accumulators, buffers and data-link logic 62 using the 100-kHz live-time clock 63.

The fast logic 54, the slow logic 55 and the 200-MHz clock 57 are digital circuits operating together to provide the pileup detection based on the fast pulse and the slow pulse. In order to operate on these pulses digitally, first they must be converted to digital form. The fast PHA 53 and the slow PHA 52 perform this function.

The fast PHA 53, which is a means for pulse-amplitude discrimination, contains 16 amplitude discriminators with monotonically increasing thresholds and outputs labeled FD1 through FD16 in FIG. 3. The outputs from the four lowest-energy discriminators called FD1, FD2, FD3 and FD4 in FIG. 3 enter the fast logic 54. The remaining 12 outputs are applied to the slow logic 55. The slow logic 55 also receives the outputs from the 36 discriminators which are contained in the slow PHA 52 and which produce the outputs labeled SD1 through SD36 in FIG. 3. Stacked discriminators were used for pulse-height analysis in this embodiment because of their high speed of operation and their flexibility in the choice of thresholds, but other methods of pulse-height analysis well-known to those knowledgable in the art could be used in other embodiments of this invention.

As depicted in FIG. 3, the slow PHA 52 also produces the sampled pulse, whose amplitude an external pulse-height analyzer (PHA) 56 can digitize. This scheme permits the operation of the discriminators to be monitored in order to check their performance and to measure their thresholds. The existence of this device in the embodiment of FIG. 3 is not intended to limit the scope of this invention.

Included within the slow PHA 52, the fast PHA 53, the fast logic 54, the slow logic 55 and the 200-MHz clock 57 are means for indicating the presence of a plurality of pulses exceeding an adaptable amplitude threshold, amplitude-correlation means and means for pulse-width measurement. These means which individually or in combination constitute this invention are all employed in the embodiment shown in FIG. 3.

The means for indicating a plurality of pulses exceeding an adaptable amplitude threshold includes multiple-pulse-detection means which operates on the outputs FD1, FD2, FD3 and FD4 from the fast PHA 53. This means has a separate pair of flip-flops forming a 2-bit shift register in the fast logic 54 for FD2, FD3 and FD4, which have amplitude thresholds corresponding to energies above that of the threshold of FD1. A positive-going transition on FD1 starts a timing sequence based on the output from the 200-MHz clock 57, and during this sequence various signals interrogate the status of the 2-bit shift registers connected to FD2, FD3 and FD4. If any of these counters receives two or more pulses before the pulse-height analysis of the slow pulse is complete, this fact is stored and sent to the slow logic 55 as a potential indicator of pulse pileup. After the slow logic 55 operating with the slow PHA 52 and the slow amplifiers 50 to form a means for determining the detector-signal amplitude has determined the event amplitude, detection-inhibiting means comprising gates contained in the slow logic 55 may cause multiple pulses on FD2 and possibly also on FD3 to be ignored. This gating function permits the threshold for multiple-pulse detection to be raised automatically for energetic events, which could otherwise falsely reject themselves as a result of fast statistical fluctuations in the photomultiplier 45 current.

The slow logic 55 also contains digital-logic means, which is a part of the amplitude-correlation means and which includes 13 two-input gates with one input logically connected to FD4 through FD16, inclusive. These gates provide an output signal which permits the slow logic 55 to accept an event for further analysis only if the status of the outputs of the fast PHA 53 and of the slow PHA 52 are consistent with a single event having produced both signals. This amplitude correlation is obtained by connecting the other input of these gates to a 13-element element subset of the 36 discriminator outputs of the slow PHA 52 in such a manner that the event is accepted only if the corresponding fast-PHA 53 output is also high whenever one of the 13 slow-PHA 52 outputs used for amplitude correlation is high. Thus the fast pulse must exceed a specific value which depends on the measured amplitude of the slow pulse. The appropriate choice of discriminator thresholds can then insure that the maximum permissible difference in the fast- and slow-pulse amplitudes cannot exceed to any great extent that value which is expected from statistical variations.

The fast PHA 53, the fast logic 54, the slow PHA 52, the slow logic 55 and the 200-MHz clock 57 also contain means for pulse-width measurement. This means uses the clock signal as a time base for measuring the width of FD1, which the pulse-amplitude discriminator in the fast PHA 53 with the lowest energy threshold produces. In the fast logic 54 of the embodiment shown in FIG. 3, gating means which passes pulses from the 200-MHz clock 57, which is one embodiment of a clock-pulse-generating means, only when FD1 is high controls the input to a counting means within the fast logic 54. This counting means includes a binary ripple counter in the embodiment of FIG. 3. When FD1 returns low after the fast pulse falls once again below the lowest discriminator threshold, the number of gated clock pulses which the counter has received represents the width of the FD1 pulse. Then means for determining excessive pulse width, which includes within the fast logic 54 additional gates decoding the state of the binary ripple counter, permits the fast logic 54 to determine if the fast pulse exceeded one or more width thresholds. This information is then sent to the slow logic 55, which uses additional gates as part of a means for width-threshold selection to choose the correct width threshold based on the measured amplitude of the slow pulse as provided by the slow PHA 52. If a second gating means within the slow logic 55 indicates that the width of the fast pulse exceeded this particular threshold, then pulse pileup contaminated the analysis, and the event will be rejected.

The implementation of the principles of this invention is not limited to the specific polarities, circuits, digital operations and pulse shapes described above. For example, the amplitude-correlation means could include a delay line and a differencing amplifier connected together in such a manner that the peak values of the slow and fast pulses were compared directly by subtraction; this difference signal could then be applied to a discriminator, which could also have an amplitude-dependent threshold. Furthermore, the width of the fast pulse could be compared with the width of a second pulse generated by a monostable multivibrator (single-shot) in order to determine if the fast pulse was too wide to have been generated by a single event. Moreover, a slower pulse can be compared with a faster second pulse generated by differentiating the slower pulse one or more times in order to produce a pulse more sensitive to event-arrival time, and the amplitudes of these pulses can be compared to check amplitude correlation and the existence of multiple fast pulses. Finally, the threshold of the discriminator used by the means for indicating a plurality of pulses could be raised after the peak amplitude of the fast pulse has been determined by injecting a voltage or current signal into the reference determining the triggering threshold. All of these implementations of the principles of this invention, together with other techniques well-known to those skilled in the art, form a part of this invention.

What I claim as new is:

1. In an apparatus for the on-line analysis of the composition of a bulk substance, wherein said analysis includes the production and capture of neutrons and the detection and measurement of the energy spectrum of the resulting capture gamma rays, an improvement for reducing the deleterious effects of pulse pileup, the improvement comprising, in combination:

(a) a gamma-ray detector operably associated with the bulk substance which is exposed to neutrons to generate capture gamma rays, the detector producing electrical signals indicative of the energies of the gamma rays to provide for the measurement of their energy spectrum;
    (b) slow-amplifier means connected to the output of the gamma-ray detector, the slow-amplifier means producing a pulse of sufficient width that satisfactory resolution can be obtained in the energy-spectrum measurement;
    (c) fast-amplifier means also connected to the output of the gamma-ray detector, the fast-amplifier means producing a pulse with a width chosen to optimize the detection of pulse pileup; and
    (d) amplitude-correlation means connected to the outputs of the slow-amplifier means and of the fast-amplifier means, the amplitude-correlation means detecting an event where the amplitude of the pulse produced by the slow-amplifier means is inconsistent with the amplitude of the pulse produced by the fast-amplifier means, whereby events with pulse amplitudes which pileup has distorted can be eliminated from the measurement of the energy spectrum of the capture gamma rays.

2. The apparatus of claim 1, above, wherein the amplitude-correlation means comprises first means for pulse-amplitude discrimination, the first means being connected to the output of the fast-amplifier means in order to indicate when the output pulse from the fast-amplifier means exceeds any one of a plurality of amplitude thresholds, whereby the amplitude of the output pulse from the fast-amplifier means can be known within the limits defined by the thresholds of the first means for pulse-amplitude discrimination.

3. The apparatus of claim 2, above, wherein the amplitude-correlation means further comprises second means for pulse-amplitude discrimination, the second means being connected to the output of the slow-amplifier means in order to indicate when the output pulse from the slow-amplifier means exceeds any one of a plurality of amplitude thresholds, whereby the amplitude of the output pulse from the slow-amplifier means can be known within the limits defined by the thresholds of the second means for pulse-amplitude discrimination.

4. The apparatus of claim 3, above, wherein the amplitude-correlation means further comprises digital-logic means connected to the outputs of the first and second means for pulse-amplitude discrimination, the digital-logic means indicating those events for which the outputs of the first and second means for pulse-amplitude discrimination are inconsistent with a single output pulse from the gamma-ray detector, whereby pulse pileup can be detected.

5. The apparatus of claim 1, above, further comprising means for pulse-width measurement connected to the output of the fast-amplifier means, the width-measuring means producing an electrical signal which is indicative of the width of the pulse at the output of the fast-amplifier means, whereby events for which pulse pileup causes the pulse from the fast-amplifier means to be lengthened excessively can be detected.

6. The apparatus of claim 1, above, further comprising means for indicating the presence of a plurality of pulses exceeding an amplitude threshold during a known time interval following the first pulse exceeding said threshold, the means for indicating the presence of a plurality of pulses being connected to the output of the fast-amplifier means, whereby events including more than one pulse during the interval necessary to perform the energy measurement can be detected.

7. The apparatus of claim 5, above, further comprising means for indicating the presence of a plurality of pulses exceeding an amplitude threshold during a known time interval following the first pulse exceeding said threshold, the means for indicating the presence of a plurality of pulses being connected to the output of the fast-amplifier means, whereby events including more than one pulse during the interval necessary to perform the energy measurement can be detected.

8. In an apparatus for the on-line analysis of the composition of a bulk substance, wherein said analysis includes the production and capture of neutrons and the detection and measurement of the energy spectrum of the resulting capture gamma rays, an improvement for reducing the deleterious effects of pulse pileup, the improvement comprising, in combination;

(a) a gamma-ray detector operably associated with the bulk substance which is exposed to neutrons to generate capture gamma rays, the detector producing electrical signals indicative of the energies of the gamma rays to provide for the measurement of their energy spectrum;

(b) fast-amplitude means connected to the output of the gamma-ray detector, the fast-amplifier means producing a pulse with a width chosen to optimize the detection of pulse pileup; and (c) means for pulse-width measurement connected to the output of the fast-amplifier means, the width-measuring means producing an electrical signal which is indicative of the width of the pulse at the output of the fast-amplifier means, whereby events for which pulse pileup causes the pulse from the fast-amplifier means to be lengthened excessively can be rejected in order to reduce in the measurement of the energy spectrum of the capture gamma rays the number of events with amplitudes which pileup has distorted.

9. The apparatus of claim 8, above, further comprising means for determining excessive pulse width connected to the output of the means for pulse-width measurement, whereby pulse pileup can be detected.

10. The apparatus of claim 9, above, wherein the means for determining excessive pulse width has a variable threshold depending on pulse amplitude.

11. The apparatus of claim 8, above, wherein the means for pulse-width measurement comprises:

(a) a pulse-amplitude discriminator connected to the output of the fast-amplifier means, the discriminator producing at its output one digital state whenever the output pulse from the fast-amplifier means exceeds the discriminator threshold and the other digital state whenever the fast-amplifier output does not exceed the threshold;

(b) gating means with a first input connected to the output of the pulse-amplitude discriminator, the output of the gating means responding to its other inputs only when the pulse-amplitude discriminator indicates that the output pulse from the fast-amplifier means exceeds the discriminator threshold;

(c) clock-pulse-generating means connected to a second input of the gating means, the clock-pulse-generating means producing pulses at a known frequency; and (d) counting means connected to the output of the gating means, the counting means determining the number of clock pulses which passed through the gating means during the interval when the output pulse from the fast-amplifier means exceeded the discriminator threshold, whereby a digital signal is generated which is indicative of the width of the output pulse from the fast-amplifier means.

12. The apparatus of claim 11, above, further comprising second gating means connected to the outputs from the counting means, the second gating means producing a digital signal whenever the counting means receives more than a given number of clock pulses, whereby pulses with widths exceeding a given threshold can be detected.

13. The apparatus of claim 12, above, wherein the second gating means comprises a plurality of thresholds for the number of clock pulses received by the counting means, the apparatus further comprising means for width-threshold selection connected to the second gating means, the means for width-threshold selection selecting the threshold for pileup detection based on the pulse amplitude, whereby the pulse-width threshold for pileup detection can be optimized at a plurality of pulse amplitudes.

14. The apparatus of claim 8, above, further comprising:

(a) slow-amplifier means connected to the output of the gamma-ray detector, the slow-amplifier means producing a pulse of sufficient width that satisfactory resolution can be obtained in the energy-spectrum measurement; and (b) amplitude-correlation means connected to the outputs of the slow-amplifier means and the fast-aamplifier means, the amplitude-correlation means detecting an event where the amplitude of the pulse produced by the slow-amplifier means is inconsistent with the amplitude of the pule produced by the fast-amplifier means, whereby pulse-pileup detection can be improved.

15. The apparatus of claim 8, above, further comprising means for indicating the presence of a plurality of pulses exceeding an amplitude threshold during a known time interval following the first pulse exceeding said threshold, the means for indicating the presence of a plurality of pulses being connected to the output of the fast-amplifier means, whereby events including more than one pulse during the interval necessary to perform the energy measurement can be detected.

16. The apparatus of claim 14, above, further comprising means for indicating the presence of a plurality of pulses exceeding an amplitude threshold during a known time interval following the first pulse exceeding said threshold, the means for indicating the presence of a plurality of pulses being connected to the output of the fast-amplifier means, whereby events including more than one pulse during the interval necessary to perform the energy measurement can be detected.

17. In an apparatus for the on-line analysis of the composition of a bulk substance, wherein said analysis includes the production and capture of neutrons and the detection and measurement of the energy spectrum of the resulting capture gamma rays, an improvement for reducing the deleterious effects of pulse pileup, the improvement comprising, in combination:
 (a) a gamma-ray detector operably associated with the bulk substance which is exposed to neutrons to generate capture gamma rays, the detector producing electrical signals indicative of the energies of the gamma rays to provide for the measurement of their energy spectrum;
 (b) fast-amplifier means connected to the output of the gamma-ray detector, the fast-amplifier means producing a pulse with a width chosen to optimize the detection of pulse pileup; and
 (c) means for indicating the presence of a plurality of pulses exceeding an amplitude threshold during a known time interval following the first pulse exceeding said threshold, wherein the threshold depends upon the measured pulse amplitude, the means for indicating the presence of a plurality of pulses being connected to the output of the fast-amplifier means,
 whereby events including more than one pulse during the interval necessary to perform the energy measurement can be detected in order to reduce in the measurement of the energy spectrum of the capture gamma rays the number of events with amplitudes which pileup has distorted.

18. The apparatus of claim 17, above, wherein the means for indicating the presence of a plurality of pulses exceeding a variable amplitude threshold comprises:
 (a) first means for pulse-amplitude discrimination connected to the output of the fast-amplifier means, the first means producing a plurality of output signals whenever the output pulse from the fast-amplifier means exceeds a plurality of amplitude thresholds;
 (b) multiple-pulse-detection means connected to the plurality of outputs of the first means for pulse-amplitude discrimination, the multiple-pulse-detection means producing a separate output signal for each output from the first means for pulse-amplitude discrimination which has two or more pulses occuring within a known time after the first detected pulse;
 (c) means operably associated with the gamma-ray detector for determining the amplitude of the signal at the detector output; and
 (d) detection-inhibiting means connected to the outputs from the multiple-pulse-detection means and to the output of the means for determining the amplitude of the detector signal, the detection-inhibiting means causing multiple pulses corresponding to specific amplitude thresholds depending on the amplitude of the signal at the detector output to be ignored,
 whereby the amplitude threshold for multiple-pulse detection can be changed based on the measured signal amplitude.

19. The apparatus of claim 18, above, wherein the means for determining the amplitude of the signal at the detector output comprises:
 (a) slow-amplifier means connected to the output of the gamma-ray detector, the slow-amplifier means producing a pulse of sufficient width that satisfactory resolution can be obtained in the energy-spectrum measurement; and
 (b) second means for pulse-amplitude discrimination connected to the output of the slow-amplifier means, the second means indicating when the output pulse from the slow-amplifier means exceeds any one of a plurality of amplitude thresholds,
 whereby the amplitude of the output signal from the detector can be known within the limits defined by the thresholds of the second means for pulse-amplitude discrimination.

20. The apparatus of claim 17, above, wherein the amplitude threshold for multiple-pulse detection changes after a signal from the gamma-ray detector has been registered.

21. The apparatus of claim 17, above, further comprising:
 (a) slow-amplifier means connected to the output of the gamma-ray detector, the slow-amplifier means producing a pulse of sufficient width that satisfactory resolution can be obtained in the energy-spectrum measurement; and
 (b) amplitude-correlation means connected to the outputs of the slow-amplifier means and of the fast-amplifier means, the amplitude-correlation means detecting an event where the amplitude of the pulse produced by the slow-amplifier means is inconsistent with the amplitude of the pulse produced by the fast-amplifier means,
 whereby pulse-pileup detection can be improved.

22. The apparatus of claim 17, above, further comprising means for pulse-width measurement connected to the output of the fast-amplifier means, the width-measuring means producing an electrical signal which is indicative of the width of the pulse at the output of the fast-amplifier means,
 whereby events for which pulse pileup causes the pulse from the fast-amplifier means to be lengthened excessively can be detected.

23. The apparatus of claim 21, above, further comprising means for pulse-width measurement connected to the output of the fast-amplifier means, the width-measuring means producing an electrical signal which is indicative of the width of the pulse at the output of the fast-amplifier means,
 whereby events for which pulse-pileup causes the pulse from the fast-amplifier means to be lengthened excessively can be detected.

* * * * *